United States Patent [19]
Hu et al.

[11] Patent Number: 6,110,109
[45] Date of Patent: Aug. 29, 2000

[54] SYSTEM AND METHOD FOR PREDICTING DISEASE ONSET

[75] Inventors: Guizhou Hu, Durham; Martin M. Root, Pittsboro, both of N.C.

[73] Assignee: Biosignia, Inc., Chapel Hill, N.C.

[21] Appl. No.: 09/277,257

[22] Filed: Mar. 26, 1999

[51] Int. Cl.$^7$ ..................................................... A61B 5/00
[52] U.S. Cl. ........................ 600/300; 128/920; 128/923
[58] Field of Search .......................... 600/300; 128/920, 128/923–924

[56] References Cited

U.S. PATENT DOCUMENTS

| | | |
|---|---|---|
| 4,733,354 | 3/1988 | Potter et al. . |
| 4,975,840 | 12/1990 | DeTore et al. . |
| 5,083,571 | 1/1992 | Prichep . |
| 5,130,936 | 7/1992 | Sheppard et al. . |
| 5,224,035 | 6/1993 | Yamashita et al. . |
| 5,265,244 | 11/1993 | Ghosh et al. . |
| 5,343,390 | 8/1994 | Doi et al. . |
| 5,359,700 | 10/1994 | Seligson . |
| 5,463,548 | 10/1995 | Asada et al. ............................ 600/300 |
| 5,687,716 | 11/1997 | Kaufmann et al. . |
| 5,692,501 | 12/1997 | Minturn . |
| 5,769,074 | 6/1998 | Barnhill et al. ......................... 600/300 |
| 5,862,304 | 1/1999 | Ravdin et al. ............................ 395/22 |
| 5,888,507 | 3/1999 | Burkly ................................ 424/130.1 |

FOREIGN PATENT DOCUMENTS

| | | |
|---|---|---|
| WO 93/12255 | 6/1993 | WIPO . |
| WO 96/12187 | 4/1996 | WIPO . |

OTHER PUBLICATIONS

W.B. Kannel, E.D. Eaker, Psychosocial and other features of coronary heart disease: insights from the Framingham Study, Am. Heart Journ. 112:1066–1073, 1986.

D.J.P Barker, Fetal orgins of coronary heart disease, Brit. Med. Journ., 311: 171–174, 1995.

(List continued on next page.)

*Primary Examiner*—Cary O'Connor
*Assistant Examiner*—Ryan Carter
*Attorney, Agent, or Firm*—Kenyon & Kenyon

[57] ABSTRACT

A method and apparatus for assessing a person's disease status is provided using a plurality of disease prediction factors for that person and applying a multivariate disease prediction equation to the data to assess the disease status of that person. The multivariate disease prediction equation includes the contribution for each disease prediction factor in a comprehensive set of disease prediction factors. Each of the plurality of disease prediction factors for which data are available from the test person is included in the comprehensive set. The multivariate disease prediction equation is obtained by (a) obtaining disease association data for each disease prediction factor in a first subset of the comprehensive set of disease prediction factors that are used in the multivariate disease prediction equation;

(b) obtaining additional disease association data for each disease prediction factor in at least one additional subset of the comprehensive set of disease prediction factors;

(c) obtaining cross-correlation data between each of the disease prediction factors in the comprehensive set, the cross-correlation data being obtained from a database in which all of the disease prediction factors in the comprehensive set are included; and (d) using the disease association data together with the cross-correlation data to develop the multivariate disease prediction equation.

30 Claims, 3 Drawing Sheets

OTHER PUBLICATIONS

C.H.D. Fall et al., Relation of infant feeding to adult serum cholesterol concentration and death from ischaemic heart disease, Brit. Med. Journ., 304: 801–801, 1992.

Faris, R.A. and Campbell, T.C., Permanently altered chemical carcinogen metabolism as related to the neonata environment, Science 211:719–721, 1981.

Rodriguez et al., "A Computer Program for Application of Epidemiological Analysis," Eur. J. Epidemiol. 1993, 9 (11) 1–4.

J.W. Furlong et al., "Neural Network Analyhsis of Serial Cardiac Enzyme Data: A Clinical Application of Artificial Machine Intelligence", Amer. J. Clinical Pathology, vol. 96, No. 1, Jul, 1991, pp. 134–141.

M.L. Astion et al., "Application of Neural Networks to the Interpretation of Laboratory Data in Cancer Diagnosis", Clinical Chemistry, vol. 38, No. 1, 1992, pp. 34–38.

P. Wilding et al., "Application of Backpropagation Neural Networks to Diagnosis of Breast and Ovarian Cancer", Cancer Letters, vol. 77, 1994, pp. 145–153.

G. Reibnegger et al., "Neural Networks as a Tool for Utilizing Laboratory Information: Comparison with Linear Discriminant Analysis and Cwith Classification and Regression Trees", Proceedings of the National Academy of Sciences,m vol. 88, Dec., 1991, pp. 114126–11430.

Encyclopedia of Statistical Sciences, edited by Samuel Kotz, Norman L. Johnson, and Campbell B. Read, published by John Wiley & Sons, 1985, Correlation Analysis (vol. 2, pp. 193–204).

Encyclopedia of Statistical Sciences, edited by Samuel Kotz, Norman L. Johnson, and Campbell B. Read, published by John Wiley & Sons, 1985, Logistic Regression Analysis (vol. 5, pp. 128–133).

Encyclopedia of Statistical Sciences, edited by Samuel Kotz, Norman L. Johnson, and Campbell B. Read, published by John wiley & Sons, 1985, Mixed Model Analysis (vol. 3, pp. 137–141, article "Fixed–, Random–, and Mixed–Effect Models").

Encyclopedia of Statistical Sciences, edited by Samuel Kotz, Norman L. Johnxon, and Campbell B. Read, published by John Wiley & Sons, 1985, Discriminant Analysis ( vol. 2, pp. 389–397).

Tangen, Catherine M., and Helms, Ronald W., (1996), "A case study of the analysis of multivariate longitudinal data using mixed (random effects) models," (Abstract) presented at the 1996 Spring Meeting of the International Biometric Society, Eastern North American Region, Richmond, Virginia, Mar., 1996.

Grady, J. J. and Helms, R. W. (1995), "Model Selection Technoques for the Covariance Matrix for Incomplete Longitudinal Data." Statistics in Medicine, 14, 1397–1416.

K.M. Anderson et al., "An Updated Coronary Risk Profile," AHA Medical/Scientific Statement 356, vol. 83, No. 1, Jan., 1991.

SYSTEM AND METHOD FOR PREDICTING DISEASE ONSET

FIELD OF THE INVENTION

The present invention relates to predicting disease onset. More particularly, the present invention relates to using the combined contribution of multiple disease factors to predict onset of a particular disease in an individual wherein the contributions are obtained from separate studies.

BACKGROUND OF THE INVENTION

One of the important tasks in medicine is to create useful statistical models for the prediction of disease. Research in this area typically involves conducting follow-up studies among populations in which the potential disease predictors are measured before the subjects experience a disease event, that is, a morbidity or even a mortality event. After the disease event, statistical procedures are used to quantify the relation between the predictors and the onset of the disease. Because of the great variation among human subjects, a study of this kind usually requires compiling a large sample size in order to create a meaningful prediction model. Studies of this nature also require careful design, well-controlled follow up and standardized predictor and disease outcome assessment. In brief, in addition to the extended time periods, considerable scientific and economic resources are required to conduct such studies.

Furthermore, it has long been known that more than one factor typically contributes to a certain disease, and often a correlation exists between these factors. For example, it has long been known that both obesity and fat consumption contribute to heart disease, and that there is a correlation between obesity and fat consumption. Thus, since diseases are typically caused by multiple factors, a meaningful prediction model needs to clearly and accurately reflect the contribution of each of these multiple factors. In the past, however, individual disease factors have typically been studied to determine how the individual disease factors independently contribute to the probability of getting a certain disease.

If the combined effect of various factors that contribute to disease risk is desired, then a study can be organized to concurrently measure each of these independent factors. A suitable multivariate regression equation, or its equivalent, can then be developed to combine these independent factors into an equation of the form $$Y = a + \Sigma b_i X_i \quad (I)$$

where Y represents disease outcome (e.g., the probability of getting coronary heart disease); the constant "a" represents the disease outcome level when all disease prediction factors are equal to zero; $X_i$ represents the disease prediction factor (e.g., smoking, drinking, blood pressure, cholesterol levels, etc.); and $b_i$, the partial regression coefficient, represents how much each factor contributes to disease outcome. The partial regression coefficient may be viewed as a weighting factor. This process may be performed to diagnose the existence of a current disease as well as to predict future disease onset.

Many studies of this kind have been carried out in the last decade or so. For example, the Framingham Heart Disease Study, which started in the 1960's and is still on-going, involves two generations of study participants that total roughly 6000 subjects. One of the publications of this study is reported in Keaven Anderson et al., *"An Updated Coronary Risk Profile—A Statement for Health Professionals"*, Circulation 83:356–62 (1991), and is incorporated by reference in its entirety. These types of studies have provided some helpful disease prediction tools. For example, the Framingham study produced a prediction equation for coronary heart disease (CHD) that has been widely used by physicians. This study is generally believed to be one of the best available prediction models. The disease prediction factors in the equation included age, blood pressure, smoking, cholesterol level, diabetes and ECG-left ventricular hypertrophy. The prediction equation has been estimated to account for about 60–70% of CHD among the general population. There have been, however, many other studies reporting risk factors for CHD that were not included in the Framingham prediction equation. Examples of such risk factors that are not included are family history, plasma fibrinogen, serum C-reactive protein, serum albumin, leukocyte count, serum homocysteine and physical exercise. One study reported that a single homocysteine measurement might be able to account for 10% of CHD risk.

Although the ongoing Framingham-type study could start collecting data on the newly identified risk factors for use in the prediction equation, it could take another 5 to 10 years to get a new and useful updated equation since, with conventional statistical methods, to estimate the partial regression coefficients, dependent variable Y and all independent variables X must be measured in the same study. Thus, the Framingham predication equation is slowly becoming outdated, and a virtual cornucopia of many new studies showing the association of CHD with still other individual risk factors are continuously appearing. Furthermore, as each currently unknown risk factor becomes identified in the future, new studies including the additional risk factors would need to be undertaken once again, since the ultimate goal is to create an equation of the form of equation I wherein all known risk factors that provide an independent contribution to disease risk are included.

It would, therefore, be desirable to conduct studies in which data are collected on a comprehensive list of all known disease prediction factors, since such studies, in addition to determining the independent contribution of each known risk factor, could also detect the synergistic contribution of multiple risk factors. Moreover, it would also be desirable to collect data, such as disclosed in co-pending Ser. No. 08/800,314, on as many other potentially significant risk factors as possible and then include the data in the same database, so that new risk factors could be identified and included in ever more powerful prediction models. In addition, it would be desirable to conduct these studies longitudinally, that is, with periodic data collection for each risk factor from the same individuals in a test population, over a long period of time. Then, also as disclosed in Ser. No. 08/800,314, the data on each risk factor for each individual in the study could be retained in the database so that the database would have the capability of including changes in an individual's disease prediction factors to develop the overall disease prediction equation.

However, because of the huge cost and large amount of time required to conduct and complete each new study involving the newly discovered risk factors, and because substantial amounts of meaningful data are already available, it would be desirable to have disease prediction models that make more effective use of the currently available data even while awaiting the results from the more comprehensive prediction models such as disclosed in Ser. No. 08/800,314. Unfortunately, for the data already available from separate studies, which each involve a limited and different subset of the known risk factors, but which in combination may include all currently known risk factors, there seems to be no method available for incorporating all the data of the comprehensive set of known risk factors into a single equation of the form of equation I.

The difficulties with the traditional methodologies may be illustrated in terms of a pair of very simple examples using hypothetical data. In one case, there is a study that compares systolic blood pressure as a function of age, body-mass-index (BMI) and cholesterol level. The problem is to determine how systolic blood pressure can be predicted as a simultaneous function of all three factors. If a study is undertaken that measures systolic blood pressure as a function of all three factors, then a prediction model of the form (systolic blood pressure)=$a+b_1$(age)+$b_2$(BMI)+$b_3$(cholesterol)

can be created by solving for each $b_i$ (i=1 to 3).

To create this model, a study is performed on a large population of N subjects (typically greater than 1,000 subjects). For each subject in the study, systolic blood pressure is measured and tabulated along with that subject's age, BMI and cholesterol level. The results of this hypothetical study are tabulated in a matrix, such as can be seen in Table 1.

TABLE 1

| SUBJECT | AGE | BMI | CHOLESTEROL LEVEL | SYSTOLIC BLOOD PRESSURE |
|---|---|---|---|---|
| 1 | 35 | 27 | 150 | 120 |
| 2 | 42 | 26 | 212 | 150 |
| — | — | — | — | — |
| N | — | — | — | — |

In this matrix, subject number 1 is 35 years old with a BMI of 27 (Kg/m$^2$), a cholesterol level of 150 (mg/dl) and a systolic blood pressure of 120 (mm Hg). Subject number 2 is 42 years old with a BMI of 26, a cholesterol level of 212, and a systolic blood pressure of 150. These measurements are taken for all N subjects in the population. Once the matrix is complete, the following equation is solved using general linear regression:

$$b=(X'X)^{-1}X'Y \quad \text{(II)}$$

where X is the N by 4 matrix of disease prediction factors (in this case, a column of 1, which represents the intercept "a", plus the columns of age, BMI and cholesterol level in Table 1) Y is an N-dimensional outcome vector (in this case, Y is the right-most column in Table 1), and b is the 4-dimensional regression-coefficient vector, a, $b_1$, $b_2$ and $b_3$. It is clear from the above that all values for the X and Y matrices are needed in order to calculate the b vector. Thus, to use this traditional methodology, one study must be performed that measures the correlation of all risk factors with a particular disease or medical condition.

Consider, as another example, the case in which a study shows that the odds of a smoker getting lung cancer is 15 times higher than for a nonsmoker, and another study shows that the odds of getting lung cancer for a person who does not consume adequate quantities of yellow vegetables is 10 times higher than a yellow-vegetable consumer. Based on these raw results standing alone, no known way exists to determine the relative contributions of both factors, and neither of these studies allows for estimating the contribution to disease risk simultaneously from both independent factors. This is because, absent a study that accounts for and measures every disease risk factor for a given disease, there is no way to know how the individual factors correlate with one another.

Since most diseases are typically correlated with a continuously growing list of several risk factors, the cost and time required for conducting such studies rapidly becomes prohibitively expensive. The net result is that such studies, though large in number, tend to be limited to an incomplete list of known risk factors for a specific disease or medical condition.

As a simple example to illustrate another aspect of the problem, assume that there is a study that measures the effects of age on coronary heart disease, and there is another study that measures the effects of cholesterol level and BMI on coronary heart disease. Additionally, assume for the purposes of simplicity, which is clearly not the case, that these are the only three known factors that contribute to coronary heart disease. This leads to two equations of the following form:

$$Y=a_1+b_{age}X_1,$$

and $$Y=a_2+b_{chol}X_2+b_{BMI}X_3$$

where $X_1$ is age, $X_2$ is cholesterol level and $X_3$ is BMI. Each individual b represents how much that factor (e.g., age) contributes to disease onset, as measured by that study.

It is very difficult to combine these equations in any meaningful way to get an equation of the form:

$$Y=a+b_1X_1+b_2X_2+b_3X_3$$

(where $b_i$ does not necessarily equal $b_{age}$, $b_{chol}$ and $b_{BMI}$, respectively), because these studies, standing alone, provide no data on the correlation between each $X_i$. In other words, from the above two equations, there appear to have been no methods disclosed that combine the results so as to quantify how age, cholesterol level and BMI jointly relate to coronary heart disease. Thus, there are few comprehensive models for predicting future disease onset and diagnosing disease status based on all known risk factors. Additionally, the existing models are not as accurate as they could be in predicting disease onset or disease status since they typically include only a limited number of the known risk factors.

The present invention is directed toward the problem of making more effective use of the currently available data, as well as providing a means for integrating newly acquired data in future studies of newly discovered risk factors, into a single comprehensive multivariate disease prediction equation.

SUMMARY OF THE INVENTION

The present invention is directed to a method and apparatus for assessing a person's disease status by obtaining data on a plurality of disease prediction factors for that person, selecting a multivariate disease prediction equation for assessing disease status for a specified disease, and applying the multivariate disease prediction equation to the data to determine the disease status of that person. The multivariate disease prediction equation includes the contribution for each disease prediction factor that is included within a comprehensive set of disease prediction factors. A comprehensive set of disease prediction factors is used herein to refer to a set that includes most, if not all, of the disease prediction factors that are known to provide an independent and statistically significant contribution to a specified disease status. Each of the plurality of disease prediction factors for which data are available from the test person is included in the comprehensive set. However, data may not necessarily be available for all known disease prediction factors for the test person, since it may not be practical or convenient to obtain all such data from the test person.

The multivariate disease prediction equation is obtained by:

(a) obtaining disease association data for each disease prediction factor in a first subset of the comprehensive set of disease prediction factors that are used in the multivariate disease prediction equation;

(b) obtaining additional disease association data for each disease prediction factor in at least one additional subset of the comprehensive set of disease prediction factors;

(c) obtaining cross-correlation data between each of the disease prediction factors in the comprehensive set, the cross-correlation data being obtained from a database in which all of the disease prediction factors in the comprehensive set are included; and (d) using the disease association data together with the cross-correlation data to develop the multivariate disease prediction equation.

Since the objective of the present invention is to provide a disease prediction methodology based on assessing a comprehensive list of well known disease prediction factors, which have not been included in their entirety in a single study, the total number of disease prediction factors in each of the above-noted subsets of disease prediction factors would be less than the total number of known disease prediction factors, that is, less than the number of disease prediction factors in the above-noted comprehensive sets. However, each of the known disease prediction factors in the comprehensive set would be included in at least one subset. Thus, using the method and apparatus of the present invention, the entire set of disease prediction factors that are known to be correlated with the disease outcome or variable of interest may be included in the multivariate disease prediction equation by including as many additional subsets as necessary so as to include all known disease prediction factors.

DETAILED DESCRIPTION OF EMBODIMENTS OF THE INVENTION

Figure 1:
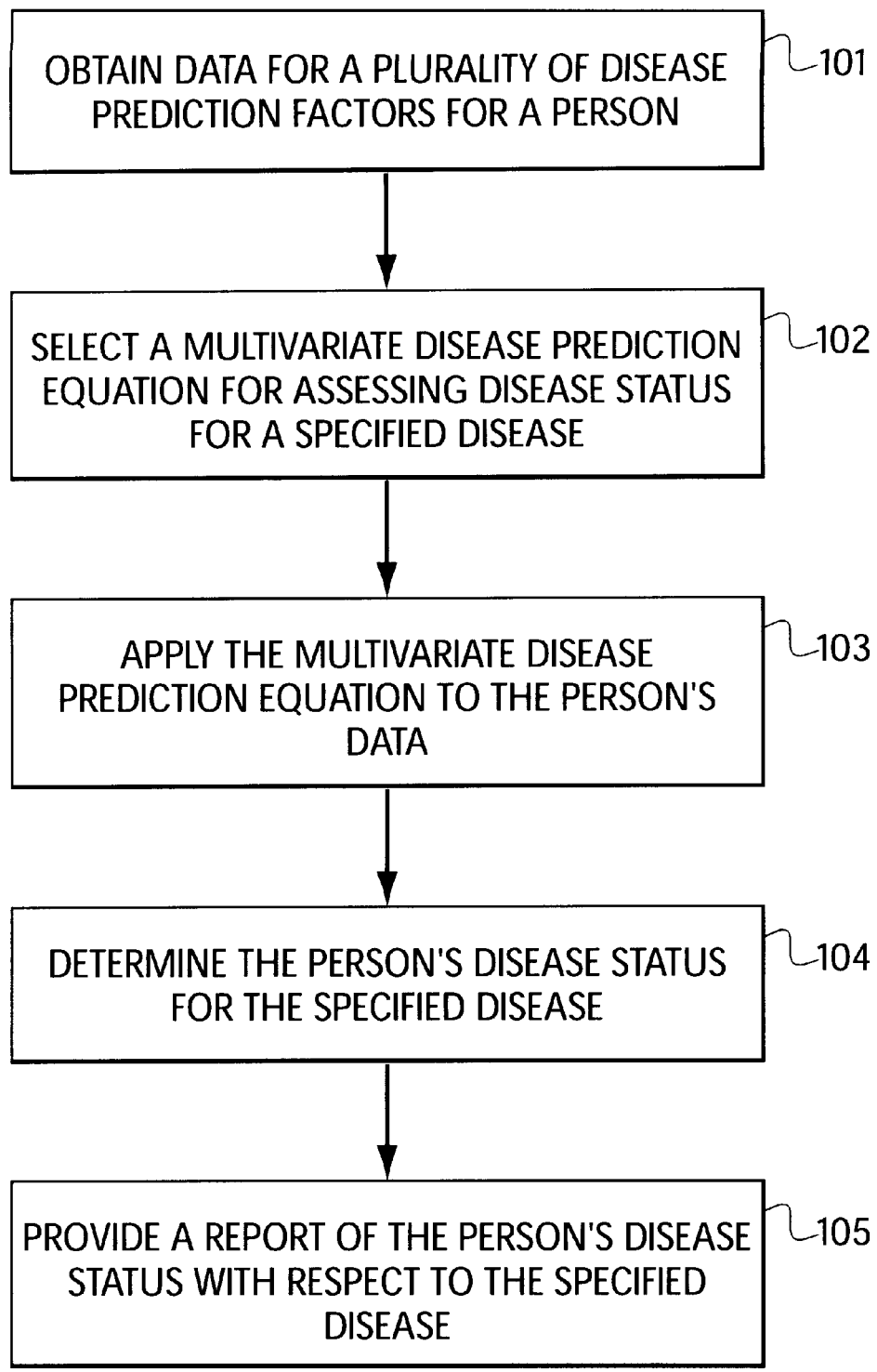
FIG. 1 shows a flow chart of a method according to the present invention for assessing disease status.

As a representative embodiment of the present invention, the disease status for a person may be assessed by obtaining data on a plurality of disease prediction factors for the person and applying a multivariate disease prediction equation to that person's data wherein the multivariate disease prediction equation may be of the form of equation I, $$Y = a + \Sigma b_i X_i \qquad (I)$$

where the disease status Y, for example, may represent a certain form of the probability of a specific future disease outcome for a specific person (e.g., the probability of getting coronary heart disease); the constant "a" represents a certain form of the probability of the specific disease status when all disease prediction factors equal zero; $X_i$ represents a quantitative value that may be assigned to each disease prediction factor for that person (e.g., with respect to smoking, drinking, blood pressure, cholesterol level, etc.); $b_i$, the partial regression coefficient, represents how much each factor contributes to disease outcome, and the summation is carried out from i=1 to i=p, the total number of disease prediction factors.

The future disease outcome may be expressed either in terms of the probability that the person will ever suffer from a specific disease outcome anytime in the future or in terms of the probability that the disease will occur within a specified time period in the future. Alternatively, the disease status Y may represent the probability that the test person currently has a specified disease, for example, low bone density, wherein diagnosis of the current condition is based on indirect measurements of risk factors correlated with the specified disease variable. In this case, a predicted value of the disease outcome variable, for example, bone density, is obtained without necessarily measuring the outcome variable itself.

The present invention is directed, in particular, toward providing a diagnosis of a specified disease onset based on combining the contributions of separate risk factors, wherein the correlation of the risk factors with the specified disease status have been established in separate studies, and the combined contribution is established based on the methodology of the present invention.

The present invention might not typically be used to diagnose a current disease status that can be more readily diagnosed by directly measuring the outcome variable itself, for example, blood pressure. More typically, when used to assess current disease status, the methodology may be used to screen for a specified current disease status based on obtaining data on a limited number of the more easily and less expensively measured risk factors. This methodology could, thus, provide a more cost effective method of assessing disease status before undertaking the more expensive and/or more time consuming tests that may typically be required to more definitively establish the actual current disease status, such as bone density.

The disease status may also be expressed as a predicted quantitative value of a specific outcome variable, for example, current or future high blood pressure. Use of the term "predicted" in this context does not necessarily mean forecasting that a specified event will occur at some point in the future, but may also be used in a statistical sense in which a disease outcome variable is predicted to have a given value within a given confidence level based on combining indirect measurements of risk factors correlated with the specified disease variable. For example, using blood pressure as the outcome variable, one may predict what the measured blood pressure would be based solely on combining indirect measurements to arrive at a "predicted" blood pressure as distinct from directly measuring blood pressure.

In each case, whether the disease status comprises onset of a future disease outcome or diagnosis of a current disease; or whether the disease status relates to a specified disease or a variable that may be correlated with a specified disease or diseases, the prediction equation is based on combining data on as many of the known risk factors as possible, or practically convenient, so as to assess a person's current disease status.

The present methodology, in particular, provides a means for incorporating newly acquired disease association data with previously known disease association data so as to develop a continuously updated multivariate disease prediction equation that includes all the known or more reliable disease prediction factors. Since the newly acquired disease association data may be directed to disease prediction factors that are themselves correlated with the previously known disease prediction factors, the present methodology specifically includes a step that distinguishes between the contribution of the newly discovered disease prediction factor that was already inherently included in the existing disease prediction equation and the additional contribution that was not included in the previously existing equation.

For example, if the newly acquired disease association data are directed to a newly discovered disease prediction factor having a very strong correlation with the known disease prediction factors, then very little additional information may be provided by the new data. However, if the newly discovered disease prediction factor has very little correlation with any of the known disease prediction factors, a substantial additional contribution to a person's disease risk may be incorporated into the multivariate disease prediction equation whenever this newly discovered disease prediction factor is included in the equation.

The present methodology provides a means for incorporating only the additional contribution of each newly discovered disease prediction factor. This is achieved by obtaining cross-correlation data between each of the disease prediction factors in the comprehensive set of disease prediction factors, the cross-correlation data being obtained from a database in which all the disease prediction factors in the comprehensive set are included; and using the disease association data together with the cross-correlation data to develop the multivariate disease prediction equation.

In a representative embodiment of the present invention, the disease association data for each disease prediction factor may be available only in the form of a univariate regression equation such that each subset of disease prediction factors may be considered as being comprised of a single disease prediction factor. The present methodology provides means for developing a multivariate regression equation based on these univariate regression coefficients.

As another representative embodiment of the present invention, data may be available from a single study correlating the disease outcome of interest with several known disease prediction factors, for example, the six factors such as used in the disease prediction equation of the Framingham CHD study. There may also exist several additional studies wherein a single disease prediction factor was evaluated and associated with the disease outcome of interest, in this case, CHD. In this case, the association data from the first subset of six factors may already be available in the form of equation I. However, in view of the newly acquired disease association data, the prediction equation is based on an incomplete set of the known disease prediction factors. The disease association data on newly discovered disease prediction factors may be incorporated into the prediction equation using a variety of techniques that fall with the scope of the present methodology. For example, for the Framingham study in which the first subset already includes six disease prediction factors, the association data are already available in the form of a multivariate regression equation and the association data for each of the newly discovered disease prediction factors are available, in the form of a univariate regression equation.

Consider, as another representative example, the above-noted case where the odds of getting lung cancer from heavy smoking is 15 fold as reported by one study, while the odds of getting lung cancer from inadequate intake of yellow vegetables in another study is 10 fold. Presently, it cannot be determined whether the overall odds for the simultaneous effects of both factors (a smoker who also has inadequate intake of yellow vegetable) is the sum of 10 and 15 or whether it is some other function. Neither study allows for estimation of the contribution to disease risk of both independent factors.

In each case, the present invention provides a methodology for combining these separate findings in such a way as to demonstrate or estimate their aggregate effects. To do this, it is necessary to know the extent to which these independent factors, when acting simultaneously, are correlated with one another, because each factor may be acting in some way to account for, or to confound, the effects of another factor. The invention allows for the collection of data on the effects of each of the independent factors, from separate studies, then to assess the correlation among the independent factors from a third source. The invention provides for applying a statistical procedure to the data to assess the simultaneous effects of each independent variable on the outcome.

With the lung cancer example, the invented method not only estimates the simultaneous effect of smoking and vegetable intake on lung cancer risk but also the independent effect of smoking and vegetable intake when the other variable is controlled or compensated. Since the independent association of each risk factor with disease outcome is usually of primary interest in such studies, researchers will therefore be very interested in knowing how much the risk of lung cancer is accounted for by one factor while holding the other constant, or vice versa.

One assumption underlying the invention is that the correlation among the independent variables, the "cross-correlation data," that are acquired from a third source is the same as, or at least similar to, the correlation among each individual study population from where the univariate associations were derived. If the correlation among independent variables has some biological basis, this assumption will be met. For example, it is reasonable to assume that the correlation between blood pressure and obesity, the two independent risk factors for diabetes, are at least very similar across different populations. For this invention, the correlation information between the variables can be derived from some third source or empirical study.

For the purposes of the present invention, the following terminology is used.

DEPENDENT VARIABLE: expressed as Y in this application, this variable is also termed the outcome variable or the response variable, and may represent disease status. The disease status may either be a probability of getting a disease event or a quantitative value of a disease-related variable, such as blood pressure or bone density.

INDEPENDENT VARIABLE: expressed as X in this application, this variable is also termed the exposure variable or explanatory variable, and represents a factor for contributing to a certain disease.

CORRELATION: this term is an expression of the strength of the statistical-based relationship between two or more variables.

REGRESSION: this term refers to the tendency of the outcome variable Y to vary with exposure variable X in a systematic fashion.

GENERAL LINEAR REGRESSION: this terms refers to a statistical method used for analyzing a linear relationship between a continuous outcome variable and a set of exposure variables.

LOGISTIC REGRESSION: this term refers to a statistical method used for analyzing a relationship between a binary or dichotomous outcome variable and a set of exposure variables.

There are a variety of embodiments for performing the present invention, based on the nature of the outcome variable (i.e., based on the type of disease status studied) and the nature of the disease prediction factors. In one embodiment, it is assumed that the outcome variable (e.g., disease status) is a continuous variable. Examples of continuous variables include, but are not limited to, blood pressure and cholesterol level. Variables like blood pressure can be considered measures of disease status, and so any model that uses these types of variables as outcome variables can be used to predict disease status. An example of a dichotomous variable (i.e., a discontinuous variable for which a condition either exists or does not exist) include a disease onset event.

The various embodiments are best understood in the form of examples from which the general form of the embodiments can be extracted and discussed.

Linear Regression

As a representative example, consider the case in which the outcome variable is a continuous variable like blood pressure. Using prior-art techniques, it is necessary to have one study that measures blood pressure as a function of all three factors so that the matrix X and outcome vector Y, discussed above, can be used to calculated the partial-regression coefficients b. It is these partial-linear-regression coefficients that represent the contribution of the various disease factors. Assume for the purposes of the example that no such single study exists. Rather, assume that there is a study that compares systolic blood pressure as a function of cholesterol level. In addition, assume that there is another study that compares blood pressure with both age and body-mass index (BMI). The first equation is of the form $$(\text{systolic blood pressure}) = a_1 + b_{chol}(\text{cholesterol})$$

the second equation is of the form:

$$(\text{systolic blood pressure}) = a_2 + b_{age}(\text{age}) + b_{BMI}(\text{BMI})$$

The data for the second equation are represented in Table 2, below.

TABLE 2

| SUBJECT | SYSTOLIC BLOOD PRESSURE | CHOLESTEROL LEVEL |
|---------|-------------------------|-------------------|
| 1       | 120                     | 160               |
| 2       | 130                     | 190               |
| —       | —                       | —                 |
| N       | —                       | —                 |

As can be seen in this table, subject 1 has systolic blood pressure of 120 and a cholesterol level of 160; subject 2 has a systolic blood pressure of 130 and a cholesterol level of 190.

The data for the second equation are represented in Table 3, below.

TABLE 3

| SUBJECT | SYSTOLIC BLOOD PRESSURE | AGE | BMI |
|---------|-------------------------|-----|-----|
| 1       | 120                     | 20  | 21  |
| 2       | 130                     | 25  | 25  |
| —       | —                       | —   | —   |
| N       | —                       | —   | —   |

As can be seen in this table, subject 1 has systolic blood pressure of 120, is 20 years old, and has a BMI of 21; subject 2 has a systolic blood pressure of 130, is 25 years old, and has a BMI of 25.

As shown above, the first blood pressure vs. cholesterol level equation is a univariate regression equation wherein $b_{chol}$ is $b_{u1}$ and $a_1$ is $a_{u1}$. However, the $a_2$, $b_{age}$ and $b_{BMI}$ in the second equation are not univariate regression coefficients, but with the data in Table 3, the univariate regression coefficients for age ($b_{u2}$) and for BMI ($b_{u3}$) can be derived along with the corresponding constant terms ($a_{u2}$ and $a_{u3}$). The three univariate regression equations can be expressed as follows:

$$Y = a_{u1} + b_{u1}(\text{cholesterol}),$$

$$Y = a_{u2} + b_{u2}(\text{age}); \text{ and}$$

$$Y = a_{u3} + b_{u3}(\text{BMI})$$

As discussed above, what is desired is an equation of the form:

$$(\text{systolic blood pressure}) = a + b_1(\text{cholesterol}) + b_2(\text{age}) + b_3(\text{BMI})$$

but unlike the prior art, there is no one study that compiles all the necessary information. Thus, more information is needed about the correlation among the three factors. To get this correlation information, one can look to the literature to see if such a study exists. An example of an existing study that provides correlation data is the Third National Health and Nutritional Examination Survey (NHANES III). From the NHANES III study, data are compiled for a variety of factors for a large population. The data are then used to calculate, again using known methods, the correlation among the various factors.

Assuming, for the sake of this example, that a study exists showing the cross correlation between the independent variables, in this case, age, BMI and cholesterol level, then the data would be collected for every subject in a study, and tabulated in a table such as table 4.

TABLE 4

| SUBJECT | AGE | BMI | CHOLESTEROL LEVEL |
|---------|-----|-----|-------------------|
| 1       | 25  | 23  | 140               |
| 2       | 32  | 30  | 160               |
| —       | —   | —   | —                 |
| N       | —   | —   | —                 |

Note that disease outcome, in this case blood pressure, is presumed not to have been measured in these studies. Correlation studies such as these may typically be referred to as "snapshot" or cross-sectional studies, that is, data are collected for each subject at a given time, and compiled as above. Of course, if disease outcome is known for these three factors, then prior art methods may be used to create a disease-prediction model.

From the data in Table 4, a correlation among the factors can be calculated using any known method, and is tabulated in a correlation matrix such as Table 5, below.

TABLE 5

|  | AGE | BMI | CHOLESTEROL LEVEL |
|---|---|---|---|
| AGE | 1 | 0.75 | 0.82 |
| BMI | 0.75 | 1 | 0.68 |
| CHOLESTEROL LEVEL | 0.82 | 0.68 | 1 |

As can be seen from Table 5, the correlation matrix, is a symmetric matrix. In this example, the correlation matrix that displays the cross correlation between age, BMI and cholesterol level forms a symmetric 3 by 3 matrix.

From the data in Table 4, a vector of standard deviation of age, BMI and cholesterol level can be calculated using any known method. In the example, $S_1=10$ (age), $S_2=2.5$ (BMI), and $S_3=45$ (cholesterol level).

Once the correlation matrix and the vector of standard deviation are known, the multivariate regression coefficients can be calculated to provide a disease prediction equation that includes each disease prediction factor. The regression coefficients for the equation can be calculated with the following general equation:

$$b=(R^{-1}(b_u*S))/S \tag{III}$$

where b is a vector of all the partial regression coefficients, in the above example, $b_1$, $b_2$, and $b_3$;

R is a p by p correlation matrix that includes cross correlation data for all the independent variables (where p is the number of independent variables), in the above example, R is the 3 by 3 matrix of Table 2;

$b_u$ is the vector of all the univariate coefficients for each independent variable, in the above example, $b_{u1}$, $b_{u2}$, and $b_{u3}$; and S is the vector of the standard deviation of each independent variable, in the above example, $S_1$, $S_2$, and $S_3$;

* is the symbol of multiplication for the element of the matrix; and

/ is the symbol of division for the element of the matrix.

In this representative example, the disease prediction factors cholesterol level, age and BMI are the independent variables, where $b_{u1}$ represents how cholesterol level is associated with systolic blood pressure, $b_{u2}$ represents how age is associated with systolic blood pressure, and $b_{u3}$ represents how BMI is associated with systolic blood pressure. Using this equation, the vector b, which contains $b_1$, $b_2$, and $b_3$ in this example, is calculated. The entries of this vector represent the contribution of the disease factor $X_i$ with which $b_i$ is associated. Once this vector is known, the new and more accurate equation is known, and as discussed above, the equation may be of the form (systolic blood pressure)=$a+b_1$(cholesterol)+$b_2$(age)+$b_3$(BMI)

The constant "a" may be calculated using the mean of systolic blood pressure, cholesterol level, age and BMI.

This methodology may be extended to include all disease prediction factors for which the required correlation data are available, thus arriving at an equation of the form:

$$Y=a+\Sigma b_i X_i \tag{I}$$

where Y, a, $b_i$ and $X_i$ are as defined above. The required correlation data include the disease association data as well as the cross-correlation data for all the disease prediction factors.

Logistic Regression

As discussed above, disease status is often a continuous variable. However, disease status may also be a dichotomous variable. Because disease onset is typically treated as a dichotomous variable, the above method, based on linear regression techniques, cannot be used. Linear-regression techniques are only appropriate for use when the outcome variable is continuous. In the case of disease onset, because the outcome variable is dichotomous, logistic regression is used.

The logistic-regression model may be represented by an equation of the form:

$$\ln(P/(1-P))=a+\Sigma b_i X_i,$$

and the equivalent expression:

$$P=(1+\exp(-a-\Sigma b_i X_i))^{-1}$$

where

P is the probability of getting a disease;

a is the intercept;

$b_i$ are the partial regression coefficients; and $X_i$ are the disease prediction factors, or independent variables.

As with linear regression, once each $b_i$ is calculated, the disease-prediction model is known (the constant "a" can be calculated using the mean probability and the means of each $X_i$). For convenience of notation, $\ln(P/(1-P))$ is hereinafter called "logit P."

First Method

This method applies to the situation where all the independent variables (disease prediction factors) are also dichotomous. As an example using this method, assume one desires to calculate the probability of the onset of hypertension. Because one is characterized as either having hypertension or as not having hypertension, this dependent variable is dichotomous, even though the probability P of getting hypertension, is continuous. In this example, as above, for the sake of simplicity, assume that there are only the following two factors for hypertension, and they are also dichotomous: smoking and alcohol drinking.

Using prior art techniques, in order to develop a multiple logistic equation it is necessary to have one study that measures hypertension status as a function of both risk factors (smoking and alcohol drinking). Assume for the purpose of the example that no such single study exists. Rather, assume that there is a study that compares hypertension as a function of smoking status. In addition, assume there is another study that compares hypertension status with alcohol drinking status. Using the prior-art techniques, the following two univariate logistic regression equations can be derived from each study:

$$\ln(P/(1-P))=a_{u1}+b_{u1}X_1$$

$$\ln(P(1-P))=a_{u2}+b_{u2}X_2$$

P is the probability of having hypertension (Y=1);

$X_1$ represents smoking status, $X_1=1$ if smoking, $X_2=0$, otherwise;

$X_2$ represents alcohol drinking status, $X_2=1$ if drinking, $X_2=0$, otherwise.

As discussed above, what is desired is an equation of the form $$\ln(P/(1-P)) = a + b_1 X_1 + b_2 X_2,$$

but unlike the prior art, there is no one study that compiles all the necessary information. Thus, more information is needed about the correlation among the two predicting factors. Once again, NHANES III type of data may provide such information.

Assuming for the sake of this example, that a study exists showing the correlation between the two independent variables, in this case, smoking and alcohol drinking. The data are then used to calculate the following parameters:

$P(X_1, X_2)$: the probability of $X_1=1$ and $X_2=1$ (smoking and drinking);

$P(X_1, \char`\^X_2)$: the probability of $X_1=1$ and $X_2=0$ (smoking but not drinking);

$P(\char`\^X_1, X_2)$: the probability of $X_1=0$ and $X_2=1$ (not smoking but drinking);

$P(\char`\^X_1, \char`\^X_2)$: the probability of $X_1=0$ and $X_2=0$ (neither smoking nor drinking);

$P(X_1)$: the probability of $X_1=1$ (smoking rate);

$P(X_2)$: the probability of $X_2=1$ (alcohol drinking rate).

Once the above parameters along with the univariate logistic regression coefficients are known, the multivariate regression coefficients can be calculated to provide a disease prediction equation that includes both disease prediction factors. The partial logistic regression coefficients for the equation can be calculated by solving these three simultaneous equations:

$$P(X_1,X_2)/(1+\exp(-a-b_1-b_2)) + P(X_1,\char`\^X_2)/(1+\exp(-a-b_1)) + P(\char`\^X_1,X_2)/(1+\exp(-a-b_2)) + P(\char`\^X_1,\char`\^X_2)/(1+\exp(-a)) = P(Y);$$

$$P(X_1,X_2)/(1+\exp(-a-b_1-b_2)) + P(X_1,\char`\^X_2)/(1+\exp(-a-b_1)) = P(X_1)/(1+\exp(-a_{u1}-b_{u1}));$$ and $$P(X_1,X_2)/(1+\exp(-a-b_1-b_2)) + P(\char`\^X_1,X_2)/(1+\exp(-a-b_2)) = P(X_2)/(1+\exp(-a_{u2}-b_{u2})).$$

where a, $b_1$ and $b_2$ are the intercept and partial regression coefficients to be solved for;

$a_{u1}$, $b_{u1}$, $a_{u2}$ and $b_{u2}$ are the univariate intercepts and regression coefficients that are derived from individual studies that each measure a factor, such as smoking, against the probability of disease onset in a population;

P(Y) is the incidence of Y=1 in the population, where Y is the outcome variable, and in this case, P(Y) represents the incidence of hypertension;

$P(X_1, X_2)$ is the probability of $X_1=1$ and $X_2=1$, where $X_1$ and $X_2$ are the disease prediction factors, and in this case, represent smoking and alcohol drinking;

$P(X_1, \char`\^X_2)$ is the probability of $X_1=1$ and $X_2=0$ $P(\char`\^X_1, X_2)$ is the probability of $X_1=0$ and $X_2=1$ $P(\char`\^X_1, \char`\^X_2)$ is the probability of $X_1=0$ and $X_2=0$ $P(X_1)$ is the probability of $X_1=1$ $P(X_2)$ is probability of $X_2=1$ The above nonlinear equations have three unknowns: a, $b_1$ and $b_2$. With three equations, they can be solved using the known statistical methods such as the Newton iteration process.

The above simultaneous equations are constructed based on the probability multiplication theorem, which is expressed by:

$$P(A_i|A_j) * P(A_j) = P(A_i, A_j)$$

where $P(A_i|A_j)$ denotes the conditional probability of $A_i$ occurring, given that $A_j$ has occurred. $P(A_i, A_j)$ denotes the probability of both $A_i$ and $A_j$ occurring.

In logistic regression, $\ln(p/(1-p)) = a + \Sigma b_i X_i$ or $P=1/(1+\exp(-a-\Sigma b_i X_i))$. Therefore, $1/(1+\exp(-a-\Sigma b_i X_i))$ is the conditional probability of Y=1 given the value of each $X_i$.

According to the multiplication theorem, $P(X_1, X_2)/(1+\exp(-a-b_1-b_2))$ is then the probability of Y=1 and $X_1=1$ and $X_2=1$;

$P(X_1, \char`\^X_2)/(1+\exp(-a-b_1))$ is then the probability of Y=1 and $X_1=1$ and $X_2=0$;

$P(\char`\^X_1, X_2)/(1+\exp(-a-b_2))$ is then the probability of Y=1 and $X_1=0$ and $X_2=1$;

$P(\char`\^X_1, \char`\^X_2)/(1+\exp(-a))$ is then the probability of Y=1 and $X_1=0$ and $X_2=0$;

The sum of the above four components is then equal to the overall probability P(Y=1), this making the first simultaneous equation. The other two equations are constructed using the same logic. In the case of more than two independent variables, the number of equations will increase to the number of independent variables plus one.

From the above equations, it can be seen that there is no need for a single study that measures all the factors with regard to a particular disease. That is, once the partial regression coefficients are found, an appropriate model can be constructed using the equation $$P = (1 + \exp(-a - \Sigma b_i x_i))^{-1}$$

As mentioned above, this method applies to the situation where the independent variables are dichotomous, but even if the independent variable is a continuous variable, it can be broken down into quartile variables and then be further broken down into three dichotomous variables (dummy variables). In this way, the above method can still be used in such a situation, although, the more variables it has, and the more levels of each variable, the more complicated the aforementioned equations will be, and a solution becomes more and more difficult.

If all the disease factors are dichotomous, the so-called "multiplication theorem" can be used to build simultaneous equations wherein the partial regression coefficients (i.e., the contribution of the disease factors) can be calculated by solving these simultaneous equations Second Method If the independent variables are not dichotomous, or if the number of variables are too large (i.e., greater than roughly 5), then two other methods can be used to create a disease-prediction model. In one of these methods, the univariate logistic regression equations are transformed into a type of univariate linear regression equation and then the multiple linear regression equation can be calculated using the method performed above (in the section of linear regression). Finally, the multiple linear regression is transformed back to the multiple logistic regression equation which then becomes the prediction model. An external data source such as the NHANES III data are needed to do these transformations.

The following example shows how external data are used to perform the transformation. Assume, for the sake of this example, that it is desired to predict the onset of hypertension, and that age, BMI and cholesterol level are the three factors known for hypertension. In this example, data such as the NHANES III data are gathered. As discussed above, this data includes measurement of certain factors for each subject in the population. These data are tabulated as in Table 4, above.

Additional information is also gathered. First, assume for the purposes of this example that a study has been performed that measures hypertension against age, another study has been performed that measures hypertension against BMI, and a third study has been performed that measures hypertension against cholesterol level. Thus, the following three equations are known from these studies:

$$\text{logit } P = a_{u1} + b_{u1}(\text{age});$$

$$\text{logit } P = a_{u2} + b_{u2}(\text{BMI}); \text{ and}$$

$$\text{logit } P = a_{u3} + b_{u3}(\text{cholesterol});$$

where $a_{ui}$ is the intercept; and each $b_{ui}$ is a univariate logistic-regression coefficient derived from each individual study.

The external factor data (e.g., the NHANES III data) are tabulated in the following way in Table 6, with extra columns to be calculated:

TABLE 6

| SUBJECT | AGE | BMI | CHOL. | $P_1$ | $P_2$ | $P_3$ | P | LOGIT P |
|---------|-----|-----|-------|-------|-------|-------|---|---------|
| 1 | 25 | 23 | 140 | | | | | |
| 2 | 30 | 27 | 165 | | | | | |
| — | — | — | — | | | | | |
| N | — | — | — | | | | | |

Note that the first four columns represents the measured external data (e.g., the NHANES III data) for all N subjects in the studied population. Of course, if more factors are measured in a particular study, extra columns will be needed to tabulate that data.

At this point, the three equations from the study above are applied for each subject in the study tabulated in Table 6:

$$P_1 = (1 + \exp(-a_{u1} - b_{u1}(\text{age})))^{-1};$$

$$P_2 = (1 + \exp(-a_{u2} - b_{u2}(\text{BMI})))^{-1}; \text{ and}$$

$$P_3 = (1 + \exp(-a_{u3} - b_{u3}(\text{cholesterol})))^{-1}$$

$P_1$, $P_2$, and $P_3$ are calculated for each subject in the NHANES III population and placed in the table above in its proper position.

Next, using all the values of $P_1$, $P_2$, and $P_3$ from the table above, the three univariate logistic equations from the study are transformed to three univariate linear equations. To do this, an ordinary least squares (OLS) regression is run on the data for each value of $P_1$, each value of $P_2$, and each value of $P_3$, using each of $P_1$, $P_2$, and $P_3$ as a dependent variable. For each of these three OLS regressions, age, BMI and cholesterol level are used respectively as the independent variables. This regression calculates the univariate linear regression coefficients such that the following equations are now known:

$$P_1 = a_{u1}' + b_{u1}'(\text{age});$$

$$P_2 = a_{u2}' + b_{u2}'(\text{BMI}); \text{ and}$$

$$P_3 = a_{u3}' + b_{u3}'(\text{cholesterol});$$

where $b_{u1}'$, $b_{u2}'$, and $b_{u3}'$ are the univariate linear-regression coefficients, and not necessarily the same as $b_{u1}$, $b_{u2}$, and $b_{u3}$, which are univariate logistic-regression coefficients.

These three equations are now linear equations, and so can be combined into a multiple linear regression expression using the method performed above. Explicitly, the correlation matrix of the NHANES III data are calculated, thus giving R, the standard deviation of each factor in the NHANES III data are calculated, thus giving S, and the univariate linear regression coefficients $b_{u1}'$, $b_{u2}'$, and $b_{u3}'$ are known, and, thus, the multivariate linear-regression coefficients can be calculated using the equation:

$$b' = (R^{-1}(b_u * S))/S \qquad (III)$$

Once b', the partial linear-regression coefficients are known, the following linear expression is known:

$$P = a' + \Sigma b_i' X_i$$

where the constant a' is calculated using the mean probability and the mean of $X_i$.

Because of the nature of the dependent variable and independent variables, this expression must be transformed into a logistic expression. To do this, first use the partial-linear regression expression above, $P = a' + \Sigma b_i' X_i$, on each of the subjects in NHANES III, giving a value of P for each subject in the study. Then, make a logit transformation of each P (i.e., determine ln of P/(1−P)). This now gives a value of logit P for each subject in the study.

To get an equation of the form $$\text{logit } P = a + \Sigma b_i X_i,$$

the OLS regression discussed above is run using logit P as dependent variable and the three factors as independent variables. This transformation results in the logistic partial-regression coefficients $b_i$, and thus the logistic expression for hypertension onset using the three disease prediction factors discussed above. The constant "a" is calculated using the mean of logit P and the mean of $X_i$.

Finally, to refine the estimate, the following numerical-iteration technique is performed on the logit P equation. The linear partial-regression coefficients $b_i'$ are known from above. When the linear partial-regression coefficients $b_i'$ are transformed into logistic partial-regression coefficients $b_i$, the transformation is a one-way transformation because when the logistic expression is transformed back to the linear expression, the new linear $b_i'$ that results will not equal the original linear $b_i'$. The logistic partial-regression coefficients $b_i$ are then altered until, when transformed back to the linear partial-regression coefficients $b_i'$, the original $b_i'$ results. At this point, it is known that the logistic partial-regression coefficients are the correct coefficients. Thus, because the logistic partial-regression coefficients are known, the disease-prediction model is known.

For example, using only one coefficient for simplicity of explanation, assume the original linear coefficient b' equals 7. When transformed into the logistic coefficient b, it turns out in this example that b equals 2. When b is transformed back to b', the new linear coefficient b' now equals 5 rather than the original 7. In response, the logistic coefficient b is altered slightly to 3. Now when transformed back to the new linear coefficient b', it turns out that b' equals 6, still not the original 7. Again, in response, the logistic coefficient b is altered again, this time to equal 4. Now when transformed back to the new linear coefficient b', it turns out that b equals the original 7. At this point, the best value for the logistic coefficient b is known to be 4, and is used in the disease-onset model.

Third Method

There are situations in which disease-prediction models exist (such as the Framingham Prediction model discussed above) that account for several factors. These models, however, do not account for every factor. In the situation in which a model already exists, this model can be used as the basis for creating a model that accounts for factors not accounted for in the existing model. In other words, the existing model can be upgraded to account for new factors. For example, the Framingham study discussed above can be upgraded to account for more factors than it already accounts for, making the model more accurate than it now is.

To use this technique, three pieces of information are needed. First, a previously-existing model, such as the Framingham model, is needed. Second, a study is needed that measures disease outcome against a factor not accounted for in the existing model. From this study the following equation is derived:

$$\text{logit } P = a + b_u X$$

where $b_u$ is the univariate regression coefficient, and X is factor studied. Finally, population data are needed, such as the NHANES III data, that study all the factors at issue, including the unaccounted for factors.

As an example of this method, a new factor can be added to an existing model for predicting coronary heart disease (CHD). Once this new factor is added to the model, another factor can be added using the same technique. This technique can be performed over and over until any number of known factors is added to the model. For the sake of the following example, it is assumed that the existing model accounts explicitly for age and BMI, but does not account explicitly for cholesterol level.

Again, because the outcome variable is dichotomous in this example, the desired model will have the form:

$$\text{logit } P = a + \Sigma b_i X_i.$$

In this example, aside from the existing prediction model for CHD, data also exist which include age, BMI and cholesterol level for every subject in a large population. The data are analogous to the NHANES III data. The data for this example are displayed in Table 7.

TABLE 7

| SUBJECT | AGE | BMI | CHOLESTEROL LEVEL |
|---------|-----|-----|-------------------|
| 1 | 25 | 23 | 142 |
| 2 | 30 | 35 | 167 |
| — | — | — | — |
| N | — | — | — |

As seen in Table 7, subject 1 is 25 years old, has a BMI of 23, and a cholesterol level of 142. Subject 2 is 30 years old, has a BMI of 35, and has a cholesterol level of 167. The data are collected and tabulated for all N subjects in a population.

The first step in this method is to calculate, using the existing prediction model, the logit of probability $P_{existing}$ of getting coronary heart disease (CHD) in a given amount of time (e.g., 5 years) for every subject in the population in Table 7 (using age and BMI, because these are the two factors used in the existing model). This will give N logit $P_{existing}$.

In the second step, a weighted OLS regression is run on the population data with $P_{existing}*(1-P_{existing})$ as the weight, the logit of $P_{existing}$ as dependent variable, and cholesterol level as the independent variable. This step results in an equation of the following form:

$$\text{logit } P = a + b_{chol}(\text{cholesterol}),$$

where $b_{chol}$ reflects the association of cholesterol level and CHD which had been captured in the existing equation based on the colinearity of cholesterol level with the other risk factors. Because the $b_{chol}$ is calculated from a probability that originated in the existing prediction model, the $b_{chol}$ tells how much the association of cholesterol level with the true probability of getting CHD is already captured by the existing model. In other words, there is some correlation between cholesterol level and the factors already accounted for in the existing model, and this b reflects this correlation.

At this point, the univariate association between cholesterol level and the true probability of getting heart disease is known (this is represented by $b_u$ above), and the association between the cholesterol level and CHD that is capture by the existing model is known (this is represented by $b_{chol}$). Thus, there is a portion of the univariate association $b_u$ that is not captured in the existing model; this amount is called $b_{extra}$, and it is this amount that must be separated out from $b_u$ and added to the existing equation to improve the existing equation in the desired way. In one embodiment of the invention, $b_{extra}$ is calculated by subtracting $b_{chol}$ from $b_u$. Once the subtraction is done, you end up with $b_{extra}$. This amount represents association between the cholesterol level and CHD that has not been captured in the existing model. This results in an equation of the form $$\text{logit } P_{new} = a + b_{age}(\text{age}) + b_{BMI}(\text{BMI}) + b_{extra}(\text{cholesterol})$$

where $b_{extra}$ represents the extra contribution of the cholesterol level to the disease status that was not accounted for in the old model.

The method of the present invention may be illustrated with the steps shown by the flow chart in FIG. 1. In step 101, data are obtained on a plurality of disease prediction factors for a person. In step 102, a multivariate disease prediction equation for assessing disease status for a specified disease is selected. In step 103, the multivariate disease prediction equation is applied to the person's data. Based on applying this equation, the disease status of the person is determined, as exemplified in step 104. Steps 103 and 104 may in fact be combined as a single step. The multivariate disease prediction equation includes a term for quantifying the contribution to a specified disease status for each disease prediction factor in a comprehensive set of disease prediction factors. After determining the disease status, a report of the person's disease status may be prepared, such as exemplified in step 105.

The flow charts in the figures provided herein are not meant to imply an order to the various steps, since the invention may be practiced in any order that is practical. For example, one may first obtain the multivariate disease prediction equation for assessing disease status for a specified disease so as to identify the specific disease prediction factors for which data will be required.

Figure 2:
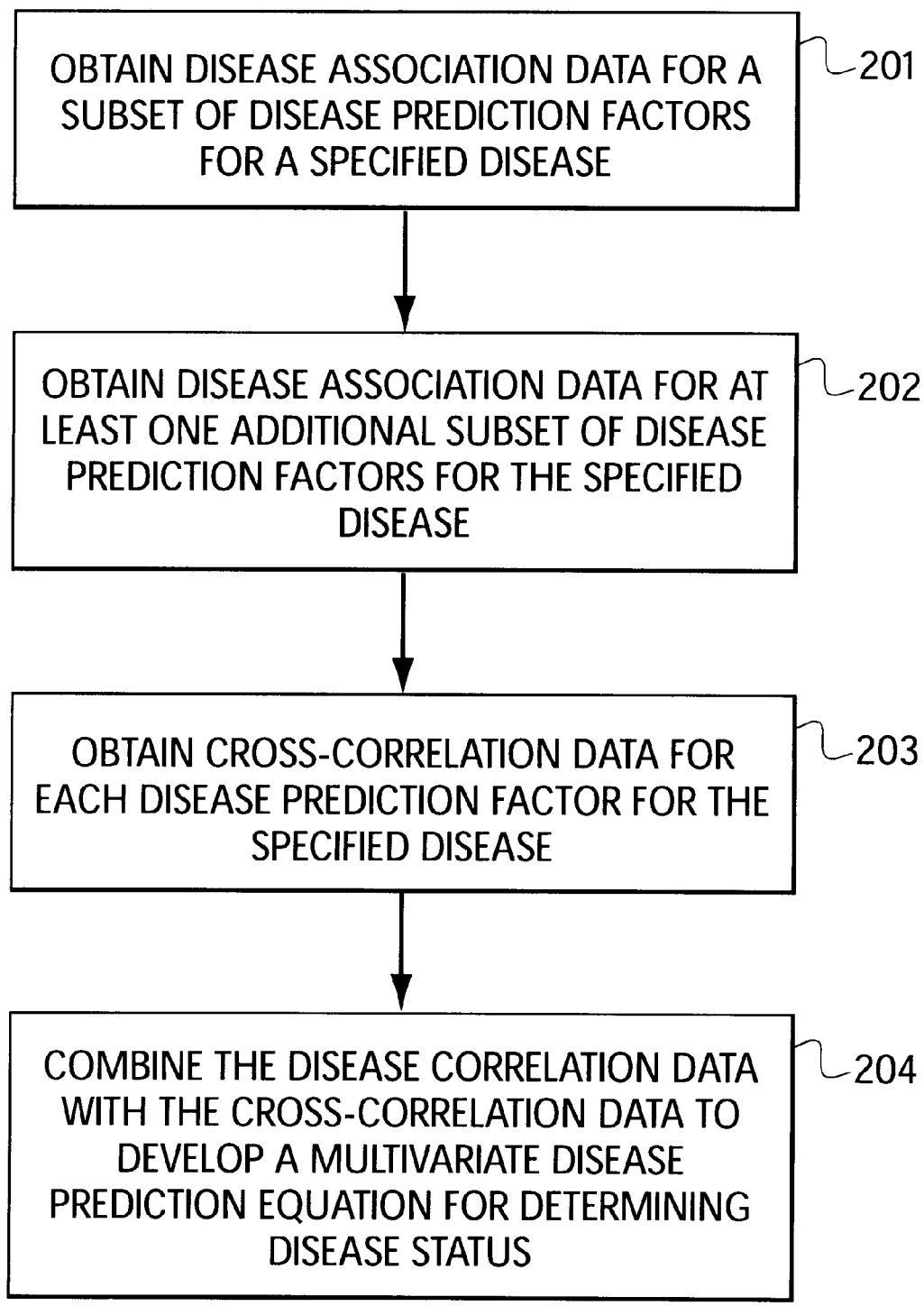
FIG. 2 shows a flow chart of a method for developing a multivariate disease prediction equation for determining disease status for a specified disease.

The multivariate disease prediction equation may be obtained by the steps shown in FIG. 2. In step 201, disease association data are obtained for each disease prediction factor in a subset of disease prediction factors. In step 202, additional disease association data are obtained for each disease prediction factor in at least one additional subset of disease prediction factors. In a representative embodiment of the present invention, each subset includes at least one disease prediction factor that is not included in any other subset. The total number of disease prediction factors in each subset is less than the total number of known disease prediction factors that form the comprehensive set of known disease prediction factors. In some cases, the subsets may include a single disease prediction factor. In step 203, cross-correlation data are obtained between each disease prediction factor in the comprehensive set. The cross-correlation data are obtained from a database in which all disease prediction factors in the comprehensive set are included. In step 204, the disease association data are used in combination with the cross-correlation data to develop the multivariate disease prediction equation.

Although the present invention is based on applying a multivariate disease prediction equation that is obtained in a prescribed manner, one would not actually need to be involved with developing the multivariate disease prediction equation in order to fall fully within the scope and spirit of practicing the present invention. For example, one could practice the present invention by selecting a multivariate disease prediction equation, which has been developed by others in accord with the methodology of the present invention, and then applying the equation to a plurality of a person's disease prediction factors to determine that person's disease status.

Figure 3:
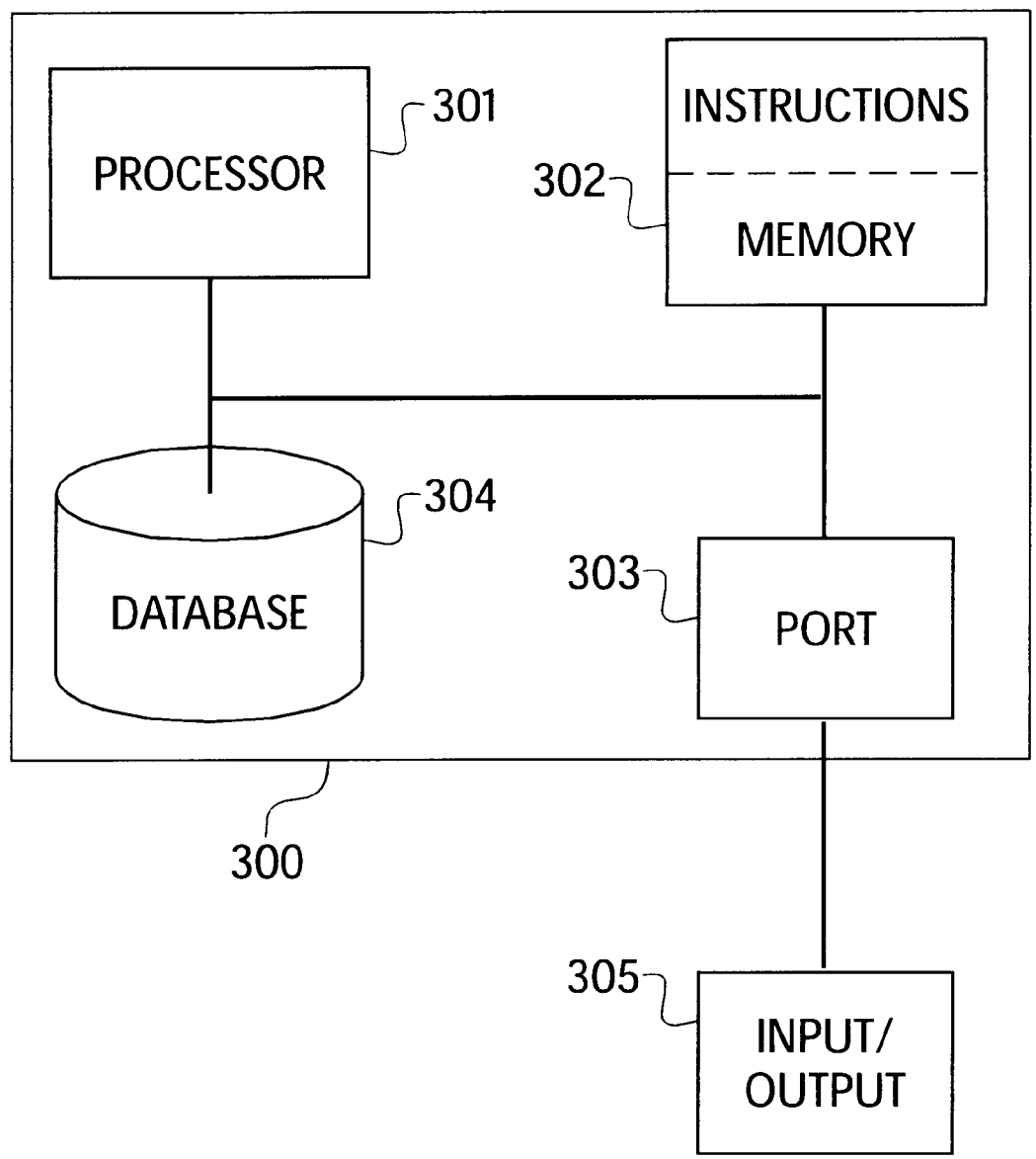
FIG. 3 shows an apparatus for assessing disease status according to the methodology of the present invention.

An apparatus for assessing disease status according to the method of the present invention is illustrated in FIG. 3. The apparatus 300 may be comprised of a processor 301 and a memory 302 coupled to the processor. The memory 302 and the processor 301 may be further coupled to a database 304 for storing data on a plurality of disease prediction factors for a person and to a port 303 for inputting or outputting data from or to an input or output transfer means 305. The memory may store instructions that are adapted to be executed by the processor using the data on the plurality of disease prediction factors to determine the disease status of the person. The instructions that are stored in the memory may include, in particular, instructions for applying the multivariate disease prediction equation that is obtained according to the methodology disclosed herein. The results may then be output through port 303.

The present invention may be further directed to the medium for storing the instructions that are used for assessing a person's disease status and that are adapted to be executed by a processor. For the purposes of this application, a memory may include any medium capable of storing instructions adapted to be executed by a processor. Some examples of such media include, but are not limited to, floppy disks, CDROM, magnetic tape, hard drives, and any other device that can store digital information. In one embodiment, the instructions are stored on the medium in a compressed and/or encrypted format. As used herein, the phrase "adapted to be executed by a processor" is meant to encompass instructions stored in a compressed and/or encrypted format, as well as instructions that have to be compiled or installed by an installer before being executed by the processor.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed is:

1. A method for assessing disease status comprising:
    obtaining data on a plurality of disease prediction factors for a person;
    selecting a multivariate disease prediction equation for assessing disease status for a specified disease; and
    applying said multivariate disease prediction equation to said data to determine the disease status of said person;
    said multivariate disease prediction equation including a term for quantifying the contribution to a specified disease status for each disease prediction factor in a comprehensive set of disease prediction factors;
    each of said plurality of disease prediction factors for said person being included in said comprehensive set; and
    said multivariate disease prediction equation being obtained by:
    (a) obtaining disease association data for each disease prediction factor in a first subset of said comprehensive set of disease prediction factors;
    (b) obtaining additional disease association data for each disease prediction factor in at least one additional subset of said comprehensive set of disease prediction factors;
    the total number of disease prediction factors in each subset being less than the total number of disease prediction factors in said comprehensive set and each of said disease prediction factors in said comprehensive set being included in at least one subset;
    (c) obtaining cross-correlation data between each of said disease prediction factors in said comprehensive set, said cross-correlation data being obtained from a database in which all of said disease prediction factors in said comprehensive set are included; and
    (d) using the disease association data together with the cross-correlation data to develop said multivariate disease prediction equation.

2. The method of claim 1, wherein said multivariate disease prediction equation is a linear regression equation and said contribution to said specified disease status comprises a linear regression coefficient for each disease prediction factor.

3. The method of claim 2, wherein said linear regression equation is of the form:

$$Y = a + \Sigma b_i X_i \qquad (I)$$

where Y represents said specified disease status;

a is a constant;

$X_i$ represents said disease prediction factors in said comprehensive set of disease prediction factors; and $b_i$ represents the partial regression coefficients for each of said disease prediction factors.

4. The method of claim 3, wherein said partial regression coefficients are obtained using an equation of the form $$b = (R^{-1}(b_u * S))/S \qquad (III)$$

where b is a vector of said partial regression coefficients for all of said disease prediction factors in said comprehensive set of disease prediction factors;

R is a p by p correlation matrix that includes cross-correlation data for all of said disease prediction factors in said comprehensive set of disease prediction factors, wherein p is the number of disease prediction factors in said comprehensive set;

$b_u$ is a vector of univariate coefficients for each of said disease prediction factors; and S is a vector of the standard deviation of each of said disease prediction factors.

5. The method of claim 1, wherein said multivariate disease prediction equation is a logistic regression equation and said contribution to said specified disease status comprises a logistic regression coefficient for each disease prediction factor.

6. The method of claim 1, wherein said multivariate disease prediction equation is of the form:

$$\ln(P/(1-P))=a+\Sigma b_i X_i$$

where P is the probability of having a specified disease status;

a is a constant;

$X_i$ represents said disease prediction factors in said comprehensive set of disease prediction factors; and $b_i$ represents the partial logistic regression coefficients for each of said disease prediction factors.

7. The method of claim 1, wherein said specified disease status comprises said person currently having a specified disease.

8. The method of claim 1, wherein said specified disease status comprises said person currently having a specified probability of a specified future disease onset.

9. The method of claim 1, wherein said specified disease status comprises a continuous variable.

10. The method in claim 1, wherein said specified disease status is a dichotomous variable.

11. An apparatus for assessing disease status comprising:

a processor;

a port coupled to said processor; and a memory coupled to said processor, said memory storing instructions adapted to be executed by said processor, said instructions including instructions for receiving data on a plurality of disease prediction factors for a person; and applying a multivariate disease prediction equation to said data to determine the disease status of said person;

said multivariate disease prediction equation including a term for quantifying the contribution to a specified disease status for each disease prediction factor in a comprehensive set of disease prediction factors;

each of said plurality of disease prediction factors for said person being included in said comprehensive set; and said multivariate disease prediction equation being obtained by:

(a) obtaining disease association data for each disease prediction factor in a first subset of said comprehensive set of disease prediction factors;

(b) obtaining additional disease association data for each disease prediction factor in at least one additional subset of said comprehensive set of disease prediction factors;

the total number of disease prediction factors in each subset being less than the total number of disease prediction factors in said comprehensive set and each of said disease prediction factors in said comprehensive set being included in at least one subset;

(c) obtaining cross-correlation data between each of said disease prediction factors in said comprehensive set, said cross-correlation data being obtained from a database in which all of said disease prediction factors in said comprehensive set are included; and (d) using the disease association data together with the cross-correlation data to develop said multivariate disease prediction equation.

12. The apparatus of claim 11, wherein said multivariate disease prediction equation is a linear regression equation and said contribution to said specified disease status comprises a linear regression coefficient for each disease prediction factor.

13. The apparatus of claim 12, wherein said linear regression equation is of the form:

$$Y=a+\Sigma b_i X_i \qquad (I)$$

where Y represents said specified disease status;

a is a constant;

$X_i$ represents said disease prediction factors in said comprehensive set of disease prediction factors; and $b_i$ represents the partial regression coefficients for each of said disease prediction factors.

14. The apparatus of claim 13, wherein said partial regression coefficients are obtained using an equation of the form $$b=(R^{-1}(b_u*S))/S \qquad (III)$$

where b is a vector of said partial regression coefficients for all of said disease prediction factors in said comprehensive set of disease prediction factors;

R is a p by p correlation matrix that includes cross-correlation data for all of said disease prediction factors in said comprehensive set of disease prediction factors, wherein p is the number of disease prediction factors in said comprehensive set;

$b_u$ is a vector of univariate coefficients for each of said disease prediction factors; and S is a vector of the standard deviation of each of said disease prediction factors.

15. The apparatus of claim 11, wherein said multivariate disease prediction equation is a logistic regression equation and said contribution to said specified disease status comprises a logistic regression coefficient for each disease prediction factor.

16. The apparatus of claim 11, wherein said multivariate disease prediction equation is of the form $$\ln(P/(1-P))=a+\Sigma b_i X_i$$

where P is the probability of having a specified disease status;

a is a constant;

$X_i$ represents said disease prediction factors in said comprehensive set of disease prediction factors; and $b_i$ represents the partial regression coefficients for each of said disease prediction factors.

17. The apparatus of claim 11, wherein said specified disease status comprises said person currently having a specified disease.

18. The apparatus of claim 11, wherein said specified disease status comprises said person currently having a specified probability of a specified future disease onset.

19. The apparatus of claim 11, wherein said specified disease status comprises a continuous variable.

20. The apparatus of claim 11, wherein said specified disease status is a dichotomous variable.

21. A medium storing instructions for assessing a person's disease status comprising a medium containing a memory storing instructions adapted to be executed by a processor, the instructions including:

receiving data on a plurality of disease prediction factors for a person; and applying a multivariate disease prediction equation to said data to determine the disease status of said person;

said multivariate disease prediction equation including a term for quantifying the contribution to a specified disease status for each disease prediction factor in a comprehensive set of disease prediction factors;

each of said plurality of disease prediction factors for said person being included in said comprehensive set; and said multivariate disease prediction equation being obtained by:

(a) obtaining disease association data for each disease prediction factor in a first subset of said comprehensive set of disease prediction factors;

(b) obtaining additional disease association data for each disease prediction factor in at least one additional subset of said comprehensive set of disease prediction factors;

the total number of disease prediction factors in each subset being less than the total number of disease prediction factors in said comprehensive set and each of said disease prediction factors in said comprehensive set being included in at least one subset;

(c) obtaining cross-correlation data between each of said disease prediction factors in said comprehensive set, said cross-correlation data being obtained from a database in which all of said disease prediction factors in said comprehensive set are included; and (d) using the disease association data together with the cross-correlation data to develop said multivariate disease prediction equation.

22. The medium of claim 21, wherein said multivariate disease prediction equation is a linear regression equation and said contribution to said specified disease status comprises a linear regression coefficient for each disease prediction factor.

23. The medium of claim 22, wherein said linear regression equation is of the form:

$$Y = a + \Sigma b_i X_i \quad (I)$$

where Y represents said specified disease status;

a is a constant;

$X_i$ represents said disease prediction factors in said comprehensive set of disease prediction factors; and $b_i$ represents the partial regression coefficients for each of said disease prediction factors.

24. The medium of claim 23, wherein said partial regression coefficients are obtained using an equation of the form $$b = (R^{-1}(b_u * S))/S \quad (III)$$

where b is a vector of said partial regression coefficients for all of said disease prediction factors in said comprehensive set of disease prediction factors;

R is a p by p correlation matrix that includes cross-correlation data for all of said disease prediction factors in said comprehensive set of disease prediction factors, wherein p is the number of disease prediction factors in said comprehensive set;

$b_u$ is a vector of univariate coefficients for each of said disease prediction factors; and S is a vector of the standard deviation of each of said disease prediction factors.

25. The medium of claim 21, wherein said multivariate disease prediction equation is a logistic regression equation and said contribution to said specified disease status comprises a logistic regression coefficient for each disease prediction factor.

26. The medium of claim 21, wherein said multivariate disease prediction equation is of the form $$\ln(P/(1-P)) = a + \Sigma b_i X_i$$

where P is the probability of having a specified disease status;

a is a constant;

$X_i$ represents said disease prediction factors in said comprehensive set of disease prediction factors; and $b_i$ represents the partial regression coefficients for each of said disease prediction factors.

27. The medium of claim 21, wherein said specified disease status comprises said person currently having a specified disease.

28. The medium of claim 21, wherein said specified disease status comprises said person currently having a specified probability of a specified future disease onset.

29. The medium of claim 21, wherein said specified disease status comprises a continuous variable.

30. The medium of claim 21, wherein said specified disease status is a dichotomous variable.

* * * * *